US009657361B2

(12) United States Patent
Munoz-Jordan et al.

(10) Patent No.: US 9,657,361 B2
(45) Date of Patent: May 23, 2017

(54) BROAD DETECTION OF DENGUE VIRUS SEROTYPES

(71) Applicants: The United States of America, as represented by the Secretary, Dept of Health and Human Services, Washington, DC (US); Jorge L. Munoz-Jordan, Puerto Rico, PR (US); Edgardo Vergne, Sabanera, PR (US); Gilberto Santiago, Guaynabo, PR (US)

(72) Inventors: Jorge L. Munoz-Jordan, Puerto Rico, PR (US); Edgardo Vergne, Sabanera, PR (US); Gilberto Santiago, Guaynabo, PR (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 310 days.

(21) Appl. No.: 14/354,972

(22) PCT Filed: Oct. 25, 2012

(86) PCT No.: PCT/US2012/061828
§ 371 (c)(1),
(2) Date: Apr. 29, 2014

(87) PCT Pub. No.: WO2013/066705
PCT Pub. Date: May 10, 2013

(65) Prior Publication Data
US 2014/0315745 A1  Oct. 23, 2014

Related U.S. Application Data

(60) Provisional application No. 61/554,126, filed on Nov. 1, 2011.

(51) Int. Cl.
*C12Q 1/70* (2006.01)
*C07H 21/04* (2006.01)
*C12Q 1/68* (2006.01)

(52) U.S. Cl.
CPC ............. *C12Q 1/701* (2013.01); *C07H 21/04* (2013.01); *C12Q 1/686* (2013.01)

(58) Field of Classification Search
None
See application file for complete search history.

(56) References Cited

U.S. PATENT DOCUMENTS

| 5,939,254 A | 8/1999 | Ennis et al. |
| 6,793,488 B1 | 9/2004 | Houng et al. |
| 2004/0126387 A1 | 7/2004 | Callahan et al. |
| 2011/0081646 A1 | 4/2011 | Carrick et al. |

FOREIGN PATENT DOCUMENTS

KR    102008000398    1/2008

OTHER PUBLICATIONS

Johnson, Barbara W. et al., Journal of Clinical Microbiology, "Serotype-specific detection of dengue viruses in a fourplex real-time reverse transcriptase PCR assay," vol. 43, No. 10, Oct. 2005, 4977-4983, ISSN 0095-1137.
Chien, Li-Jung, et al., Journal of Clinical Microbiology, "Development of real-time reverse transcriptase PCR assays to detect and serotype Dengue viruses," vol. 44, No. 4, pp. 1295-1304, Apr. 2006, ISSN 0095-1137.
Munoz-Jordan, Jorge L., et al., Journal of Clinical Microbiology, "Highly sensitive detection of dengue virus nuleic acid in samples from clinically ill patients," vol. 47, No. 4, pp. 927-931, Apr. 2009, ISSN 0095-1137.
International Search Report issued in connection with corresponding PCT application No. PCT/US2012/061828 on Feb. 1, 2013.
Lanciotti, R. et al., "Rapid Detection and Typing of Dengue Viruses from Clinical Samples by Using Reverse Transcriptase-Polymerase Chain Reaction," *Journal of Clinical Microbiology*, Mar. 1992, pp. 545-551.
Lo, C. et al., "One-Step Rapid Reverse Transcription-PCR Assay for Detecting and Typing Dengue Viruses with GC Tail and Induced Fluorescence Resonance Energy Transfer Techniques for Melting Temperature and Color Multiplexing," *Clinical Chemistry* 53:4, pp. 594-599 (2007).
Extended European Search Report for co-pending application No. 12845721.5, issued May 13, 2015.

*Primary Examiner* — David Thomas
(74) *Attorney, Agent, or Firm* — Klarquist Sparkman, LLP

(57) ABSTRACT

Processes for detecting Dengue virus (DENV) nucleic acid in a sample are provided including producing an amplification product by amplifying DENV nucleotide sequence and detection of an amplification by hybridization of a probe or other technique. The processes use primers or probes with introduced mutations and or degenerate bases that provide excellent superiority in detection and serotyping of DENV in a sample.

1 Claim, 3 Drawing Sheets

SEQUENCE LISTING

<160> NUMBER OF SEQ ID NOS: 24

<210> SEQ ID NO 1
<211> LENGTH: 20
<212> TYPE: DNA
<213> ORGANISM: Dengue virus

<400> SEQUENCE: 1
caaaaggaag tcgygcaata                                               20

<210> SEQ ID NO 2
<211> LENGTH: 24
<212> TYPE: DNA
<213> ORGANISM: Dengue virus

<400> SEQUENCE: 2
ctgagtgaat tctctctgct raac                                          24

<210> SEQ ID NO 3
<211> LENGTH: 19
<212> TYPE: DNA
<213> ORGANISM: Dengue virus

<400> SEQUENCE: 3
catgtggytg ggagcrcgc                                                19

<210> SEQ ID NO 4
<211> LENGTH: 22
<212> TYPE: DNA
<213> ORGANISM: Dengue virus

<400> SEQUENCE: 4
caggctatgg cacygtcacg at                                            22

<210> SEQ ID NO 5
<211> LENGTH: 22
<212> TYPE: DNA
<213> ORGANISM: Dengue virus

<400> SEQUENCE: 5
ccatytgcag carcaccatc tc                                            22

<210> SEQ ID NO 6
<211> LENGTH: 27
<212> TYPE: DNA
<213> ORGANISM: Dengue virus

<400> SEQUENCE: 6
ctcyccraga acgggcctcg acttcaa                                       27

<210> SEQ ID NO 7
<211> LENGTH: 20
<212> TYPE: DNA
<213> ORGANISM: Dengue virus

<400> SEQUENCE: 7
ggactrgaca cacgcaccca                                               20

<210> SEQ ID NO 8
<211> LENGTH: 26
<212> TYPE: DNA
<213> ORGANISM: Dengue virus

<400> SEQUENCE: 8
catgtctcta ccttctcgac ttgyct                                          26

<210> SEQ ID NO 9
<211> LENGTH: 26
<212> TYPE: DNA
<213> ORGANISM: Dengue virus

<400> SEQUENCE: 9
acctggatgt cggctgaagg agcttg                                          26

<210> SEQ ID NO 10
<211> LENGTH: 21
<212> TYPE: DNA
<213> ORGANISM: Dengue virus

<400> SEQUENCE: 10
ttgtcctaat gatgctrgtc g                                               21

<210> SEQ ID NO 11
<211> LENGTH: 20
<212> TYPE: DNA
<213> ORGANISM: Dengue virus

<400> SEQUENCE: 11
tccaccygag actccttcca                                                 20

<210> SEQ ID NO 12
<211> LENGTH: 26
<212> TYPE: DNA
<213> ORGANISM: Dengue virus

<400> SEQUENCE: 12
tycctacycc tacgcatcgc attccg                                          26

<210> SEQ ID NO 13
<211> LENGTH: 20
<212> TYPE: DNA
<213> ORGANISM: Dengue virus

<400> SEQUENCE: 13
caaaaggaag tcgtgcaata                                                 20

<210> SEQ ID NO 14
<211> LENGTH: 24
<212> TYPE: DNA
<213> ORGANISM: Dengue virus

<400> SEQUENCE: 14
ctgagtgaat tctctctact gaac                                            24

<210> SEQ ID NO 15
<211> LENGTH: 19
<212> TYPE: DNA
<213> ORGANISM: Dengue virus

<400> SEQUENCE: 15
catgtggttg ggagcacgc                                                  19

<210> SEQ ID NO 16
<211> LENGTH: 22
<212> TYPE: DNA
<213> ORGANISM: Dengue virus

```
<400> SEQUENCE: 16
caggttatgg cactgtcacg at                                          22

<210> SEQ ID NO 17
<211> LENGTH: 22
<212> TYPE: DNA
<213> ORGANISM: Dengue virus

<400> SEQUENCE: 17
ccatctgcag caacaccatc tc                                          22

<210> SEQ ID NO 18
<211> LENGTH: 27
<212> TYPE: DNA
<213> ORGANISM: Dengue virus

<400> SEQUENCE: 18
ctctccgaga acaggcctcg acttcaa                                     27

<210> SEQ ID NO 19
<211> LENGTH: 20
<212> TYPE: DNA
<213> ORGANISM: Dengue virus

<400> SEQUENCE: 19
ggactggaca cacgcactca                                             20

<210> SEQ ID NO 20
<211> LENGTH: 26
<212> TYPE: DNA
<213> ORGANISM: Dengue virus

<400> SEQUENCE: 20
catgtctcta ccttctcgac ttgtct                                      26

<210> SEQ ID NO 21
<211> LENGTH: 26
<212> TYPE: DNA
<213> ORGANISM: Dengue virus

<400> SEQUENCE: 21
acctggatgt cggctgaagg agcttg                                      26

<210> SEQ ID NO 22
<211> LENGTH: 21
<212> TYPE: DNA
<213> ORGANISM: Dengue virus

<400> SEQUENCE: 22
ttgtcctaat gatgctggtc g                                           21

<210> SEQ ID NO 23
<211> LENGTH: 20
<212> TYPE: DNA
<213> ORGANISM: Dengue virus

<400> SEQUENCE: 23
tccacctgag actccttcca                                             20
```

```
<210> SEQ ID NO 24
<211> LENGTH: 26
<212> TYPE: DNA
<213> ORGANISM: Dengue virus

<400> SEQUENCE: 24
ttcctactcc tacgcatcgc attccg                                          26
```

BROAD DETECTION OF DENGUE VIRUS SEROTYPES

CROSS REFERENCE TO RELATED APPLICATIONS

This application depends from and claims priority to U.S. Patent Application No. 61/554,126 filed Nov. 1, 2011, the entire contents of which are incorporated herein by reference.

GOVERNMENT INTEREST

The invention described herein may be manufactured, used, and licensed by or for the United States Government.

FIELD OF THE INVENTION

This invention relates generally to processes for detection of foreign organisms in fluid samples. More specifically, the invention relates to selective detection of dengue virus (DENV) in biological or other fluid media. Processes are described for rapid and sensitive detection and subtyping (serotyping) of DENV in biological samples and quantification thereof. Diagnostic kits are provided for detection of DENV serotypes in blood (serum or plasma) samples from patients with symptoms of dengue illness in a clinical, laboratory, or field setting.

BACKGROUND OF THE INVENTION

Dengue virus (DENV) is the cause of dengue illness (dengue fever, dengue hemorrhagic fever and dengue shock syndrome), which is reported in hundreds of thousands of people each year. Dengue hemorrhagic fever is fatal in about 0.5% of cases. DENVs are a group of four closely related arboviruses represented by serotypes DENV-1, DENV-2, DENV-3, and DENV-4. In areas of high virus presence, all four of the DENV serotypes may be circulating simultaneously.

The four DENV serotypes are antigenically distinct, but related serologically. Thus, infection by one serotype does not provide protection from subsequent infections by other serotypes. Studies demonstrated that host developed antibodies directed to the first infecting serotype may have some affinity for a second infecting serotype and lead to enhancement of the ability of the second virus to infect the host.

Patients with dengue usually seek medical attention during the first 5 days of illness; when the virus is present in the blood and IgM antibodies are not yet detectable. Therefore, diagnostic tests highly rely on the ability to detect virus components such as viral RNA.

Identification of DENV through serological methods is complicated due to extensive cross-reactivity between flaviviruses. The level of circulating IgM is not uniform based on the type of infection. For example, infection by a second DENV serotype may show little to no IgM response, and its presence may be masked by circulating IgM from either prior DENV infection, or from infection by another flavivirus. Thus, in areas with high or epidemic transmission of multiple flaviviruses, identification of DENV may not be possible by serological methods.

Within each DENV serotype, there are 4-6 genotypes, which represent lineages that may differ from one another in approximately 5-10% of their genomes.

Thus, there is a need for compositions and methods for the specific detection of DENV in fluidic samples such as whole blood, plasma, or serum early during disease presentation that does not rely on antibody serology, yet is sufficiently specific enough to broadly detect multiple DENV serotypes.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Compositions and methods are provided for superior detection of DENV in a sample such as a fluidic sample. These methods capitalize on one or more primers or probes suitable for use with an assay system capitalizing on the polymerase chain reaction that allow detection of all known viruses in a specific serotype. As such, the methods and compositions provided may be used to provide superior confidence in determining the presence or absence of a DENV virus in a sample in either a singleplex or multiplex assay format Processes are provided for detecting DENV in a sample that include producing an amplification product by amplifying a nucleotide sequence using a forward primer that hybridizes to a first region within the Dengue virus genome, and a reverse primer that hybridizes to a second region within the Dengue virus genome, under conditions suitable for a polymerase chain reaction, and optionally wherein at least one of the forward primer or reverse primer has one or more degenerate or non-wild-type nucleotide substitutions; and detecting a first detection signal correlating to the presence of the amplification product to detect the Dengue virus in a sample. A first primer optionally includes the sequence of SEQ ID NO: 1; SEQ ID NO: 4; SEQ ID NO: 7, SEQ ID NO: 10, or combinations of these primers are used. A reverse primer optionally includes the sequence of SEQ IN NO: 2; SEQ ID NO: 5; SEQ ID NO: 8, SEQ ID NO: 11, or combinations of these primers are used. A probe optionally includes the sequence of SEQ ID NO: 3; SEQ ID NO: 6; SEQ ID NO: 9, SEQ ID NO: 12, or combinations these probes are used.

Any suitable detection system can be used to detect an amplification product, even in the absence of a probe. In the absence of a probe a first detection signal is produced by the amplification product itself or by a non-probe signal directed to the amplification product. Illustratively, an amplification product is detected by gel electrophoresis, Southern blotting, liquid chromatography, mass spectrometry, liquid chromatography/mass spectrometry, mass spectrometry, static fluorescence, dynamic fluorescence, high performance liquid chromatography, ultra-high performance liquid chromatography, enzyme-linked immunoadsorbent assay, real-time PCR, nucleotide sequencing, or combinations thereof.

The compositions and processes can be used to diagnose or confirm the diagnosis of the presence or absence of DENV in a subject or confirm the presence or absence of a DENV in a sample, or for the preparation of a composition, kit, or other device that may be used to diagnose or confirm the diagnosis of the presence or absence of DENV in a subject or a sample.

The compositions and processes provided dramatically improve confidence in diagnosis or detection of DENV from one or more serotypes in a sample.

DETAILED DESCRIPTION OF EMBODIMENTS OF THE INVENTION

Figure 1A:
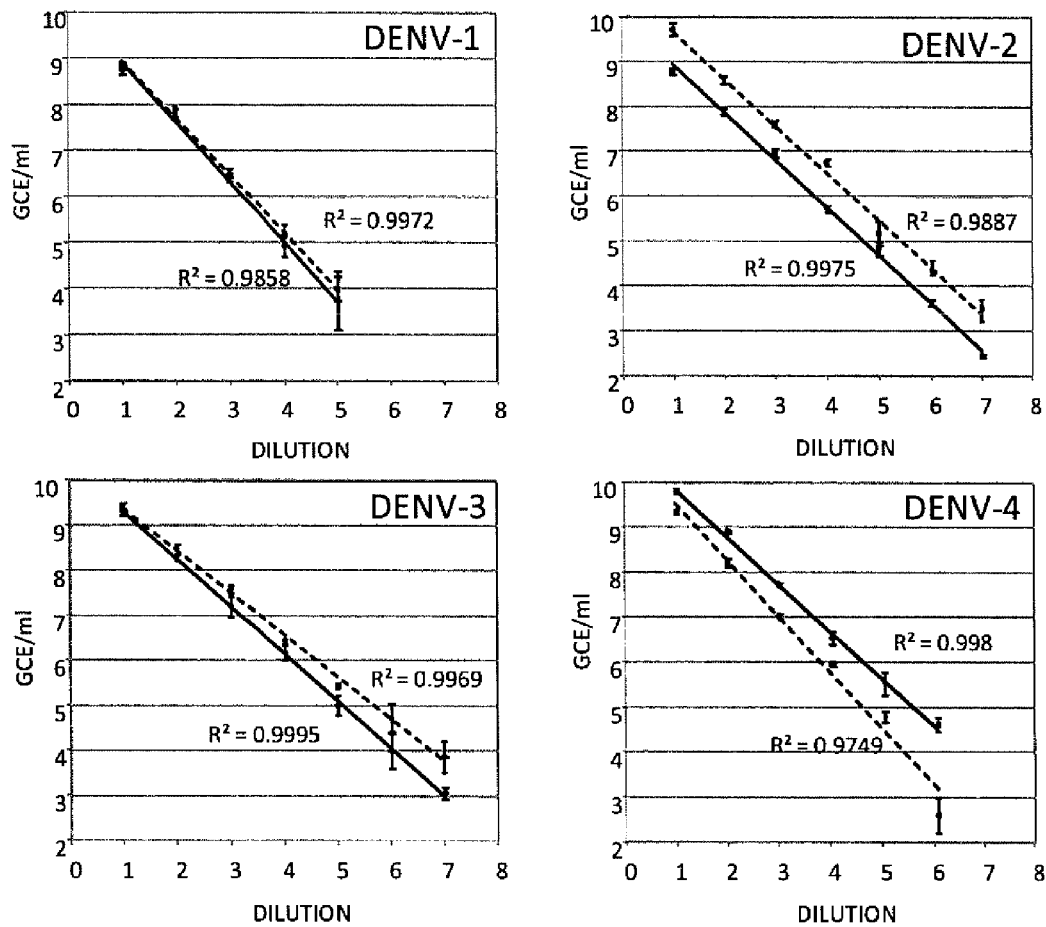
FIG. 1 illustrates DENV serotypes 1-4 specific detection as measured in genome copy equivalents per mL of sample (GCE/mL) between virus dilutions in human serum and human plasma demonstrating FIG. 1A (singleplex) and 1B (multiplex) assay formats.
Figure 1B:
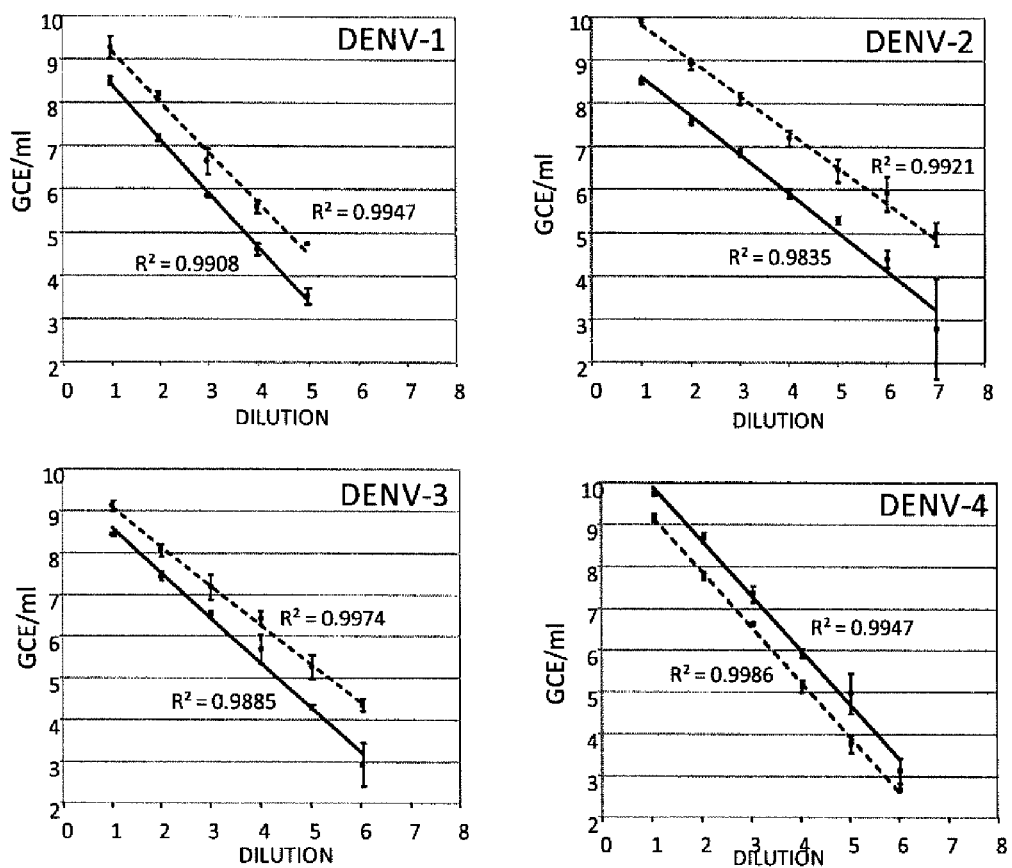

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes are described as an order of individual steps or using specific materials, it is appreciated that described steps or materials may be interchangeable such that the description of the invention includes multiple parts or steps arranged in many ways as is readily appreciated by one of skill in the art. While numerous elements of the description are directed to primers of SEQ ID NO: 1, SEQ ID NO: 2, and probe of SEQ ID NO: 3, it is appreciated that other primers or probes are substitutable as is readily appreciated by one of skill in the art as well as the inclusion of primers of SEQ ID NO: 1, SEQ ID NO: 2, and probe of SEQ ID NO: 3 in a multiplex assay along with other primers and probes.

The invention has utility for the detection of DENV in a sample. As it is currently necessary to detect DENV in clinical specimens by the standard serological methods, sensitive techniques such as RT-PCR may provide a more reliable diagnostic than other currently employed assay systems. Prior attempts at designing nucleic acid based diagnostic methods have met with limited success due to poor recognition of multiple DENV serotypes, inability to multiplex the assay, or lack of sensitivity. Despite the failings of prior investigators, the inventors identified a new family of primers and probes suitable for single or multiplexed real-time RT-PCR that are far superior to prior primer and probe sequences in their ability to amplify and detect all four DENV serotypes from multiple members of the serotypes that have sequence variations.

Compositions and methods are provided for the sensitive detection of DENV in samples, such as biological or environmental samples, using techniques involving PCR. Primers are provided that amplify regions of DENV genetic RNA with high specificity and broad DENV recognition that are subsequently detectable, optionally by sensitive detection systems.

The following definitional terms are used throughout the specification without regard to placement relative to these terms.

As used herein, the term "variant" defines either a naturally occurring genetic mutant of DENV or a recombinantly prepared variation of the DENV. The term "variant" may also refer to either a naturally occurring variation of a given encoded peptide or a recombinantly prepared variation of a given encoded peptide or protein in which one or more amino acid residues have been modified by amino acid substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative also defined as a degenerate base mimicking a C/T mix such as that from Glen Research Corporation, Sterling, Va., illustratively LNA-dA or LNA-dT, or other nucleotide modification known in the art or otherwise.

As used herein, the term "mutant" defines the presence of mutations in the nucleotide sequence of an organism as compared to a wild-type organism. A mutant is a variant.

The description of primers and probes to amplify and detect one or more target nucleic acid molecule is presented. In some embodiments, the primers, probes, or both specifically include variants, analogues, derivatives, and mutants of the sequences presented herein. In some embodiments, the primers, probes, or both specifically exclude variants, analogues, derivatives, and mutants of the sequences taught herein or the wild-type sequences.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, 95%, or more, base pair matches to each other typically remain hybridized to each other. Illustrative hybridization conditions are described in, for example but not limited to, Current Protocols in Molecular Biology, John Wiley & Sons, N.Y. (1989), 6.3.1 6.3.6; Basic Methods in Molecular Biology, Elsevier Science Publishing Co., Inc. N.Y. (1986), pp. 75 78, and 84 87; and Molecular Cloning, Cold Spring Harbor Laboratory, N.Y. (1982), pp. 387 389, and are well known to those skilled in the art. A non-limiting example of stringent hybridization conditions is hybridization in 6× sodium chloride/sodium citrate (SSC), 0.5% SDS at about 60° C. followed by one or more washes in 2×SSC, 0.5% SDS at room temperature. Another non-limiting example of stringent hybridization conditions is hybridization in 6×SSC at about 45° C. followed by one or more washes in 0.2×SSC, 0.1% SDS at 50 to 65° C. Other stringent hybridization conditions will be evident to one of ordinary skill in the art based on general knowledge in the art as well as this specification.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1%, (by dry weight) of contaminating material. When nucleotide/oligonucleotide is produced by chemical synthesis, it is optionally substantially free of chemical precursors or other chemicals, i.e., it is separated from chemical precursors or other chemicals which are involved in the synthesis of the molecule. Accordingly, such preparations of the nucleotide/oligonucleotide have less than about 30%, 20%, 10%, or 5% (by dry weight) of chemical precursors or compounds other than the nucleotide/oligonucleotide of interest. In some embodiments of the present invention, a nucleotide/oligonucleotide is isolated or purified. This terms "isolated" or "purified" are exclusive of a nucleic acid that is a member of a library that has not been purified away from other library clones containing other nucleic acid molecules.

As used herein, the term "sample" is a portion of a larger source. A sample is optionally solid, gaseous, or fluidic. A sample is illustratively an environmental or biological sample. An environmental sample is illustratively, but not limited to, water, sewage, soil, or air. A "biological sample" is as sample obtained from a biological organism, a tissue, cell, cell culture medium, or any medium suitable for mimicking biological conditions. Non-limiting examples include, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions, throat or nasal materials. In some embodiments, target agents are contained in: serum; plasma; whole blood; feces; urine; throat fluid; nasopharyngeal fluid; or other respiratory fluid.

As used herein, the term "medium" refers to any liquid or fluid sample in the presence or absence of a virus. A medium is illustratively a solid sample that has been suspended, solubilized, or otherwise combined with fluid to form a fluidic sample. Non-limiting examples include buffered saline solution, cell culture medium, acetonitrile, trifluoroacetic acid, combinations thereof, or any other fluid recognized in the art as suitable for combination with virus or other cells, or for dilution of a biological sample or amplification product for analysis.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions .times.100%). In some embodiments, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set. e.g., to score 50. wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described herein or otherwise known in the art, with or without allowing gaps. In calculating percent identity, typically only exact matches are counted.

As used herein, the terms "subject" and "patient" are synonymous and refer to a human or non-human animal, optionally a mammal including a human, a non-primate such as cows, pigs, horses, goats, sheep, cats, dogs, avian species and rodents; and a non-human primate such as monkeys, chimpanzees, and apes; and a human, also optionally denoted specifically as a "human subject".

Processes are described that provide a rapid, specific, and sensitive assay for detection of DENV in a sample by amplifying one or more nucleotide sequences of the RNA genome of DENV by processes similar to the polymerase chain reaction (PCR). Processes are similarly provided for diagnosing the presence or absence of DENV infection in a subject. The presence of DENV detected in a sample from the subject diagnoses or confirms a prior diagnosis of infection of the subject by DENV. The absence of DENV in a sample from a subject diagnoses the absence of an infection of the subject by DENV.

An oligonucleotide forward primer with a nucleotide sequence complementary to a unique sequence in a DENV nucleotide sequence is hybridized to its complementary sequence and extended. A nucleotide sequence is complementary if it hybridizes under stringent conditions. Similarly, a reverse oligonucleotide primer complementary to a second strand of DENV RNA (or reverse transcribed DNA) is hybridized and extended. The amplification products of the forward and reverse primer overlap in complementary sequence providing a uniform amplification product from each pair of forward and reverse primers. This system allows for amplification of specific nucleic acid sequences and is suitable for simultaneous or sequential detection systems.

The present invention relates to the use of the sequence information of DENV for diagnostic or other detection processes. In particular, the present invention provides a process for detecting the presence or absence of nucleic acid molecules of DENV, natural or artificial variants, analogs, or derivatives thereof, in a sample. In some embodiments, processes involve obtaining a biological sample from one or more of various sources and contacting the sample with a compound or an agent (e.g. primer or probe) capable of detecting a nucleic acid sequence of DENV, natural or artificial variants, analogs, or derivatives thereof, such that the presence of DENV, natural or artificial variants, analogs, or derivatives thereof, is detected in the sample. Optionally, infection by DENV is diagnosed by positively detecting one or more DENV serotypes in the sample. In some embodiments, the presence of DENV, natural or artificial variants, analogs, or derivatives thereof, is detected in the sample using a PCR reaction or real-time polymerase chain reaction (RT-PCR) including primers that are constructed based on a partial nucleotide sequence of the DENV organism with the proviso that at least one of a probe, forward primer, or reverse primer houses a sequence that is not wild-type. The inventors discovered that by introduction of non-wild-type nucleotides, and optionally one or more positions of non-wild type degeneracy, the use of the primers or probes results in much greater detection affinity than previously detectable by prior primer or probe sequences or combinations of sequences. The locations of a non-wild type nucleotide or degeneracy was surprising in that no knowledge in the art suggests that these positions or type of substitution would alter a detection assay.

Primers must be designed to amplify target from the greatest number of DENV strains while simultaneously preventing false positives. In a non-limiting embodiment, a forward primer designed to be successful for selective amplification in a PCR based assay such as in a RT-PCR process is illustratively 5'-CAAAAGGAAGTCGYG-CAATA-3' (SEQ ID NO: 1). As used herein the nucleotide notation "Y" represents a degenerate purine that is either adenine or guanine. The nucleotide notation "R" as used herein represents a degenerate pyrimidine that is either thymine or cytosine. In some embodiments for the detection of DENV-1, a reverse primer designed to be successful for selective amplification in a PCR based assay such as in a RT-PCR process is illustratively 5'-CTGAGTGAAT-TCTCTCTGCTRAAC-3' (SEQ ID NO: 2). In some embodiments, the primers used in a process are the nucleic acid sequences of SEQ ID NOs:1 and 2. As used herein, the term "amplify" is defined as producing one or more copies of a target molecule, or a complement thereof. A nucleic acid such as DNA or RNA is amplified to produce one or more amplification products. Illustratively, a forward primer and an optional reverse primer are contacted with a target under conditions suitable for a polymerase chain reaction to produce an amplification product.

An agent for detecting DENV nucleic acid sequences is optionally a labeled nucleic acid probe capable of hybridizing to a portion of the DENV genome, or amplification products derived therefrom such as DNA produced by reverse transcription of the RNA genome or a portion thereof. In some embodiments for the detection of DENV-1, the nucleic acid probe is a nucleic acid molecule of the nucleic acid sequence of 5'-CATGTG-GYTGGGAGCRCGC-3' (SEQ ID NO: 3), which sufficiently specifically hybridizes under stringent conditions to a DENV nucleic acid sequence. A probe is optionally labeled with a fluorescent molecule such as a fluorescein (FAM) molecule and optionally a quencher such as the black hole quencher BHQ1.

Primers and probes are provided for singleplex or multiplex detection of one or more serotypes of DENV in a sample. Illustrative primers and probes are provided in Table 1 where bold nucleotides represent degenerate base location or other non-wild type substitutions.

TABLE 1

| Oligonucleotide | | | SEQ ID NO: |
|---|---|---|---|
| D1-F | CDC DENV-1-4 Real Time RT-PCR | CAAAAGGAAGTCGYGCAATA | 1 |
| D1-R | CDC DENV-1-4 Real Time RT-PCR | CTGAGTGAATTCTCTCTGCTRAAC | 2 |
| D1-Probe | CDC DENV-1-4 Real Time RT-PCR | CATGTGGYTGGGAGCRCGC | 3 |
| D2-F | CDC DENV-1-4 Real Time RT-PCR | CAGGCTATGGCACYGTCACGAT | 4 |
| D2-R | CDC DENV-1-4 Real Time RT-PCR | CCATYTGCAGCARCACCATCTC | 5 |
| D2-Probe | CDC DENV-1-4 Real Time RT-PCR | CTCYCCRAGAACGGGCCTCGACTTCAA | 6 |
| D3-F | CDC DENV-1-4 Real Time RT-PCR | GGACTRGACACACGCACCCA | 7 |
| D3-R | CDC DENV-1-4 Real Time RT-PCR | CATGTCTCTACCTTCTCGACTTGYCT | 8 |
| D3-Probe | CDC DENV-1-4 Real Time RT-PCR | ACCTGGATGTCGGCTGAAGGAGCTTG | 9 |
| D4-F | CDC DENV-1-4 Real Time RT-PCR | TTGTCCTAATGATGCTRGTCG | 10 |
| D4-R | CDC DENV-1-4 Real Time RT-PCR | TCCACCYGAGACTCCTTCCA | 11 |
| D4-Probe | CDC DENV-1-4 Real Time RT-PCR | TYCCTACYCCTACGCATCGCATTCCG | 12 |

Processes optionally involve a real-time PCR assay (RT-PCR), optionally, a real-time quantitative PCR assay. In some embodiments, the PCR assay is a TaqMan assay (Holland et al., PNAS 88(16):7276 (1991)). It is appreciated that the processes are amenable to performance on other RT-PCR systems and protocols that use alternative reagents illustratively including, but not limited to Molecular Beacons probes, Scorpion probes, multiple reporters for multiplex PCR, combinations thereof, or other DNA detection systems.

The assays are performed on an instrument designed to perform such assays, for example those available from Applied Biosystems (Foster City, Calif.). In some embodiments, a real-time quantitative PCR assay is used to detect the presence of DENV, natural or artificial variants, analogs, or derivatives thereof, in a sample by subjecting the DENV nucleic acid from the sample to PCR reactions using specific primers, and detecting the amplified product using a probe. In some embodiments, the probe is a TaqMan probe which consists of an oligonucleotide with a 5'-reporter dye and a 3'-quencher dye.

A fluorescent reporter dye, such as FAM dye (illustratively 6-carboxyfluorescein), is covalently linked, optionally to the 5' end of the oligonucleotide probe. Other dyes illustratively include TAMRA, AlexaFluor dyes such as AlexaFluor 495 or 590, Cascade Blue, Marina Blue, Pacific Blue, Oregon Green, Rhodamine, Fluorescein, TET, HEX, Cy5, Cy3, and Tetramethylrhodamine. A reporter is optionally quenched by a dye at the 3' end or other non-fluorescent quencher. Quenching molecules are optionally suitably matched to the fluorescence maximum of the dye. Any suitable fluorescent probe for use in RT-PCR detection systems is illustratively operable in the instant invention. Similarly, any quenching molecule for use in RT-PCR systems is illustratively operable. In some embodiments, a 6-carboxyfluorescein reporter dye is present at the 5'-end and matched to BLACK HOLE QUENCHER (BHQ1, Biosearch Technologies, Inc., Novato, Calif.) The fluorescence signals from these reactions are captured at the end of extension steps as PCR product is generated over a range of the thermal cycles, thereby allowing the quantitative determination of the bacterial load in the sample based on an amplification plot.

The DENV nucleic acid sequences are optionally reverse transcribed and/or amplified before or simultaneous with being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art, illustratively by PCR techniques. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In some embodiments, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same or similar processes as described herein. In some examples, the Superscript II platinum One-Step RT-PCR system with the PLATINUM Taq DNA polymerase (Invitrogen Corp., Carlsbad, Calif.) is used. In any event, the processes of the invention are not to be limited to the embodiments of amplification described herein.

One process of in vitro amplification, which optionally is used according to this invention, is the polymerase chain reaction (PCR) described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention. For example, DNA is subjected to 30 to 35 cycles of amplification in a thermocycler as follows: 2 minutes at 50° C., 10 minutes at 95° C., and then 50×(15 seconds at 95° C. plus 1 minute at 60° C.).

The primers for use in amplifying the mRNA or genomic DNA of DENV may be prepared using any suitable process, such as conventional phosphotriester and phosphodiester processes or automated embodiments thereof so long as the primers are capable of hybridizing to the nucleic acid sequences of interest. One process for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the process of the invention are complementary to each strand of nucleotide sequence to be amplified. The term "complementary" means that the primers hybridize with their respective strands under conditions, which allow the agent for polymerization to function, such as stringent hybridization conditions. In other words, the primers that are complementary to the flanking sequences hybridize with the flanking sequences and permit amplification of the nucleotide sequence. Optionally, the 3' terminus of the primer that is extended is perfectly (100%) base paired with the complementary flanking strand. Probes optionally possess nucleotide sequences complementary to one or more strands of DENV. Optionally, primers contain the nucleotide sequences of SEQ ID NOs: 1 and 2. It is appreciated that the complements of SEQ ID NOs: 1 and 2 are similarly suitable for use in the instant inventions. It is further appreciated that oligonucleotide sequences that hybridize with SEQ ID NOs 1 or 2 are also similarly suitable. Finally, multiple positions are available for hybridization on DENV and will be also suitable hybridization with a probe when used with the proper forward and reverse primers.

Those of ordinary skill in the art will know of various amplification processes that can also be utilized to increase the copy number of target DENV nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., BioTechnology 3:1008 1012 (1985)), allele-specific oligonucleotide (ASO) probe analysis (Conner et al., PNAS 80: 278 (1983)), oligonucleotide ligation assays (OLAs) (Landegren et al., Science 241:1077 (1988)), RNase Protection Assay, among others. Molecular techniques for DNA analysis have been reviewed (Landegren et al, Science 242:229 237 (1988)). Following DNA amplification, the reaction product may be detected by Southern blot analysis, with or without using radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In some embodiments of the invention, one nucleoside triphosphate is radioactively labeled, thereby allowing direct visualization of the amplification product by autoradiography. In some embodiments, amplification primers are fluorescently labeled and run through an electrophoresis system. Visualization of amplified products is by light detection followed by computer assisted graphic display, without a radioactive signal.

Other methods of detection amplified oligonucleotide illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, affinity chromatography, other chromatography methods, immunoenzymatic methods (Ortiz, A and Ritter, E, *Nucleic Acids Res.*, 1996; 24:3280-3281), streptavidin-conjugated enzymes, DNA branch migration (Lishanski, A, et al., *Nucleic Acids Res.*, 2000; 28(9):e42), enzyme digestion (U.S. Pat. No. 5,580,730), colorimetric methods (Lee, K., *Biotechnology Letters,* 2003; 25:1739-1742), or combinations thereof. A detection signal is produced that is related to the detection method employed, be it RT-PCR or other detection method. A test sample optionally produces a first detection signal upon amplification of a target. A control sample optionally produces a second detection signal upon amplification of a control molecule.

The term "labeled" with regard to the probe is intended to encompass direct labeling of the probe by coupling (i.e., physically linking) a detectable substance to the probe, as well as indirect labeling of the probe by reactivity with another reagent that is directly labeled. Examples of indirect labeling include detection of a probe using a fluorescently labeled antibody and end-labeling or centrally labeling of a DNA probe with biotin such that it can be detected with fluorescently labeled streptavidin. The detection methods can be used to detect DNA, RNA, genomic nucleic acid, or amplification products thereof, in a sample in vitro as well as in vivo. For example, in vitro techniques for detection of nucleic acid include northern hybridizations, in situ hybridizations, reverse transcription-PCR, real-time-PCR, and DNase protection. In vivo techniques for detection of DENV include introducing into a subject organism a labeled antibody directed against a polypeptide component or directed against a particular nucleic acid sequence of DENV. For example, the antibody can be labeled with a radioactive marker whose presence and location in the subject organism can be detected by standard imaging techniques, including autoradiography.

The size of the primers used to amplify a portion of the nucleic acid sequence of DENV is at least 5, and often 10, 15, 20, 25, 30 or more nucleotides in length, optionally any value or range between 5 and 30 nucleotides in length. Optionally, the GC ratio is above 30%, 35%, 40%. 45%. 50%, 55%, or 60% so as to prevent hair-pin structure on the primer. The amplicon is optionally of sufficient length to be detected by standard molecular biology methodologies. The forward primer is optionally shorter than the reverse primer or vice versa. Techniques for modifying the $T_m$ of either primer are operable herein. An illustrative forward primer or reverse primer contains LNA-dA or LNA-dT (Glen Research Corporation) so as to match $T_m$ with a corresponding alternate primer.

A pair of forward and reverse primers optionally hybridize to a target that represents the same gene or product of the same gene within one or more DENV. Illustratively, SEQ ID NOs: 1 and 2 are each directed to positions in the NS5 gene. SEQ ID NOs: 4 and 5 are each directed to positions in the E gene. SEQ ID NOs: 7 and 8 are each directed to positions in the prM gene. SEQ ID NOs: 10 and 11 are each directed to positions in the prM gene. In some embodiments, the amplification product produced by a particular primer pair is unique to that DENV serotype. Illustratively, some embodiments involve a process for detecting the presence or absence multiple DENV serotypes wherein each primer pair recognizes a unique portion of the same gene or different genes within DENV.

An inventive process uses a polymerization reaction which employs a nucleic acid polymerizing enzyme, illustratively a DNA polymerase, RNA polymerase, reverse transcriptase, or mixtures thereof. It is further appreciated that accessory proteins or molecules are present to form the replication machinery. A polymerizing enzyme is optionally a thermostable polymerase or thermodegradable polymerase. Use of thermostable polymerases is well known in the art such as Taq polymerase available from Invitrogen Corporation, Carlsbad, Calif. Thermostable polymerases allow a polymerization reaction to be initiated or shut down by changing the temperature other condition in the reaction mixture without destroying activity of the polymerase.

Accuracy of the base pairing of DNA sequence amplification is provided by the specificity of the enzyme. Error rates for Taq polymerase tend to be false base incorporation of $10^{-5}$ or less. (Johnson, *Annual Reviews of Biochemistry*, 1993: 62:685-713; Kunkel, *Journal of Biological Chemistry*, 1992; 267:18251-18254). Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to the primer. When the DENV sequence is a single-stranded RNA molecule due to heat denaturing, the polymerase is bound at the primed end of the single-stranded nucleic acid at an origin of replication. A binding site for a suitable polymerase is optionally created by an accessory protein or by any primed single-stranded nucleic acid.

In some embodiments, detection of PCR products is achieved by mass spectrometry. Mass spectrometry has several advantages over real-time PCR systems in that it can be used to simultaneously detect the presence of DENV and decipher mutations in target nucleic acid sequences allowing identification and monitoring of emerging strains. Further, mass spectrometers are prevalent in the clinical laboratory. Similar to fluorescence based detection systems, mass spectrometry is capable of simultaneously detecting multiple amplification products for a multiplexed and controlled approach to accurately quantifying components of biological or environmental samples.

Multiple mass spectrometry platforms are suitable for use in the invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR (RT-PCR), gel electrophoresis, or combinations thereof.

Optionally, PCR amplification products are generated using complementary forward and reverse oligonucleotide primers. In a non-limiting example, DENV-1 genetic sequences or fragments thereof are amplified by the primer pair SEQ ID NOs: 1 and 2. The resulting amplification product is either directly detected such as by a probe, or is subsequently processed and prepared for detection by processes known in the art. It is appreciated that the complements of SEQ ID NOs: 1 and 2 are similarly suitable for use in the invention. It is further appreciated that oligonucleotide sequences that hybridize with SEQ ID NOs: 1 or 2 are also similarly suitable. Finally, multiple positions are available for hybridization on the DENV genome, or other and will be also suitable hybridization with forward and reverse primers that may or may not be used with a probe for PCR.

A primer pair is optionally SEQ ID NOs: 1 and 2, SEQ ID NOs: 4 and 5, SEQ ID NOs: 7 and 8, or SEQ ID NOs: 10 and 11.

In some embodiments, a multiplex assay or set of singleplex assays are performed. Optionally, an assay detects the presence or absence of DENV-1. Optionally, an assay detects the presence or absence of DENV-2. Optionally, an assay detects the presence or absence of DENV-3. Optionally, an assay detects the presence or absence of DENV-4. Optionally, an assay detects the presence or absence of DENV-1 and DENV-2. Optionally, an assay detects the presence or absence of DENV-1 and DENV-3. Optionally, an assay detects the presence or absence of DENV-1 and DENV-4. Optionally, an assay detects the presence or absence of DENV-2 and DENV-3. Optionally, an assay detects the presence or absence of DENV-2 and DENV-4. Optionally, an assay detects the presence or absence of DENV-3 and DENV-4. Optionally, an assay detects the presence or absence of DENV-1, DENV-2 and DENV-3. Optionally, an assay detects the presence or absence of DENV-1, DENV-2 and DENV-4. Optionally, an assay detects the presence or absence of DENV-2, DENV-3 and DENV-4. Optionally, an assay detects the presence or absence of DENV-1, DENV-3 and DENV-4. Optionally, an assay detects the presence or absence of DENV-1, DENV-2, DENV-3 and DENV-4. Optionally an assay detects the presence or absence of 1, 2, 3, or 4 serotypes selected from DENV-1, DENV-2, DENV-3 and DENV-4.

Optionally, multiple amplification products are simultaneously produced in a multiplex PCR reaction that are then available for simultaneous detection and quantification. Thus, multiple detection signals are inherently produced or emitted that are separately and uniquely detected in one or more detection systems. In some embodiments, the primer sets and probes of Table 1 are all simultaneously used in single reaction chamber in a single multiplex reaction. Optionally, the primer pairs and related probes of Table 1 are used in a plurality of singleplex reactions with each tube possessing sufficient primers and probes to recognize one or more DENV serotypes. One or more singleplex reactions are optionally performed simultaneously or sequentially. Multiple detection signals produced by multiple probes are optionally produced in parallel. Optionally, a single biological sample is subjected to analysis for the simultaneous or sequential detection of DENV genetic sequences. It is appreciated that three or more independent or overlapping sequences are simultaneously or sequentially measured in the inventive processes. Oligonucleotide matched primers (illustratively SEQ ID NOs: 1 and 2) are simultaneously or sequentially added and the biological sample, or a portion thereof, is subjected to proper thermocycling reaction parameters. For detection by mass spectrometry, a single sample of the amplification products from each gene are simultaneously analyzed allowing for rapid and accurate determination of the presence of DENV. Optionally, analysis by real-time PCR is employed capitalizing on multiple probes with unique fluorescent signatures. Thus, each gene is detected without interference by other amplification products. This multi-target approach increases confidence in quantification and provides for additional internal control.

In some embodiments, the processes further involve optionally obtaining a control sample from a control subject, contacting a control sample, optionally from said subject, with a compound or agent capable of detecting the presence of DENV nucleic acid in the sample, and comparing the presence or absence of RNA or DNA in the control sample with the presence of RNA or DNA in the test sample. A control sample is optionally a portion of a test sample processed in parallel with the test sample. A control sample is optionally a purified, isolated, or otherwise processed nucleic acid sequence of known concentration optionally including at least a portion of DENV sequence, where the nucleic acid sequence or portion thereof will hybridize under stringent conditions with a forward primer, a reverse primer, and, optionally, a probe. A control sample is used to produce a complementary amplification product produced either simultaneously with, or sequentially to the first amplification product produced from a target. The complementary amplification product is optionally detected by detecting a second detection signal by the same of a different method than that used to detect the first amplification product. Illustratively, a second amplification product is detected using a second probe of the same or of a different sequence than that use to detect the first amplification product. A second probe optionally has one or more labels that are the same or different than that of a first probe, when present. Illustratively, a control sample is subjected to the identical amplification conditions in the same or other parallel analysis, such as on the same instrument, as the test sample. If the test sample and the control sample are processed in different reaction chambers, the same probes with the same labels may be used.

Some embodiments include using a nucleic acid calibrator to produce a signal from a known quantity of sample molecule. A nucleic acid calibrator is optionally identical to or different from a target molecule. Amplification of a nucleic acid calibrator optionally produces a third detection signal, the presence of, intensity of, or size of is optionally compared to a first detection signal to quantify the amount of target, or amplification product in the test sample. Optionally, a plurality of nucleic acid calibrators are used. A plurality of nucleic acid calibrators are optionally of differing concentrations such as those suitable to produce a standard curve. The detection signal from the test sample is optionally compared to the standard curve to quantify the amount of amplification product or target in the test sample. A nucleic acid calibrator optionally includes a known amount of DENV nucleic acid sequence, or a portion of a DENV nucleic acid sequence.

Also provided are one or more kits for detecting or diagnosing DENV infection that contains reagents for the amplification, or direct detection of DENV or portions thereof in a sample. An exemplary kit optionally includes a forward and reverse primer pair, and a probe. Kits include any primer, probe, or set of primers or probes defined herein, analogues there, variants thereof, or derivatives thereof. It is further appreciated that a kit optionally includes ancillary reagents such as buffers, solvents, thermostable polymerases, nucleotides, and other reagents necessary and recognized in the art for amplification and detection of DENV in a sample.

A kit for detection of DENV infection in a subject optionally contains reagents for PCR based detection of DENV genetic sequences, either structural or non-structural, and optionally for detection of antibodies directed to DENV proteins. The components of the kits are any of the reagents described above or other necessary and non-necessary reagents known in the art for solubilization, detection, washing, storage, or other need for in a diagnostic assay kit. Suitable antibodies are known in the art.

The invention also encompasses kits for detecting the presence of DENV nucleic acids in a test sample. The kit, for example, includes a labeled compound or agent capable of detecting a nucleic acid molecule in a test sample and, in certain embodiments, for determining the quantity of DENV in the sample.

For oligonucleotide-based kits, the kit includes, for example: (1) an oligonucleotide, e.g., a detectably labeled oligonucleotide, which hybridizes to a nucleic acid sequence of DENV and/or (2) one or a pair of primers (one forward and one reverse) useful for amplifying a nucleic acid molecule containing at least a portion the DENV sequence. The kit can also include, e.g., a buffering agent, a preservative, or a protein stabilizing agent. The kit can also include components necessary for detecting the detectable agent (e.g., an enzyme or a substrate). The kit can also contain a control sample or a series of control samples which is assayed and compared to the test sample contained. Each component of the kit is usually enclosed within an individual container and all of the various containers are usually enclosed within a single package along with instructions for use.

Also provided are a library of nucleic acid primers and probes suitable for use in diagnosis of DENV infection, detection of the presence or absence of DENV in a sample, or for combination with other kits suitable for such purposes. A library optionally includes a pair of primers and a probe for detection of DENV-1. A forward primer is optionally SEQ ID NO: 1. A reverse primer is optionally SEQ ID NO: 2. A probe is optionally SEQ ID NO: 3. A library or kit optionally includes a pair of primers and a probe (s) for detection of DENV-2. A forward primer is optionally SEQ ID NO: 4. A reverse primer is optionally SEQ ID NO: 5. A probe is optionally SEQ ID NO: 6. A library optionally includes a pair of primers and a probe for detection of DENV-3. A forward primer is optionally SEQ ID NO: 7. A reverse primer is optionally SEQ ID NO: 8. A probe is optionally SEQ ID NO: 9. A library optionally includes a pair of primers and a probe for detection of DENV-4. A forward primer is optionally SEQ ID NO: 10. A reverse primer is optionally SEQ ID NO: 11. A probe is optionally SEQ ID NO: 12. A pair (or more) of forward primers, reverse primers, probes, or both with each sequence of a primer or probe of the degeneracy represented in the library or kit. Libraries or kits are provided that include a sufficient number of primers or probes to represent each degenerate nucleic acid at the indicated positions in Table 1. A kit or a library optionally includes primers or probes for DENV-1, DENV-2, DENV-3, and DENV-4, or any subgroup thereof.

The processes are amenable to use for diagnosis of DENV infection or simple detection of the presence of DENV in a subject, such as insects, and any other organism capable of infection or transfection by or with DENV.

To increase confidence and to serve as an internal or external control, a purified solution containing DENV is optionally used as a sample. Optionally, by amplification of a single sample with known quantities of DENV or of a set of samples representing a titration of DENV, the level of DENV in the unknown biological sample is determined, optionally as a control. Optionally, the purified and quantified DENV solution is analyzed in parallel with the unknown biological sample to reduce inter assay error or to serve as a standard curve for quantitation of unknown DENV in the test sample. Using purified and quantified DENV solution provides for a similar complete genetic base RNA strand for amplification.

In some embodiments, a subgenomic fragment is cloned into a plasmid for amplification, purification, and use as a quantitative comparator or nucleic acid calibrator. In a non-limiting example, a RNA fragment of DENV is optionally amplified from a positive serum sample using primers bracketing the RT-PCR target regions in DENV. The known concentration of the subgenomic fragment is used to create a standard curve for quantitative determinations and to access amplification efficiency.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to samples derived from a human, a person having ordinary skill in the art recognizes that similar techniques and other techniques known in the art readily translate the examples to other organisms. Reagents illustrated herein are commonly cross reactive between mammalian species or alternative reagents with similar properties are commercially available, and a person of ordinary skill in the art readily understands where such reagents may be obtained.

EXAMPLES

Example 1

RT-PCR Assay Design

Serotype-specific DENV primers and fluorogenic probes are designed by using a newly generated consensus sequence based on multiple new entries into the database of DENV genetic sequences. The DENV consensus sequence is entered into Primer Express 3.0 (Applied Biosystems). Each of the primers and probes is used to generate families of primers and probes with various mutations or degeneracies introduced at selected regions of the primers or probes. Every primer and probe is aligned to the corresponding serotype alignment and the frequency of every base in the oligonucleotide is determined. Mismatches between prior primers/probes and the sequence alignments are attended to as follows: degeneracy is introduced in a given nucleotide position when mismatch is 40% or greater between 2 or more strains; a base is replaced by another fixed base when mismatch is 90% or greater between 2 or more strains in a given position. International Union of Pure and Applied Chemistry (IUPAC) codes are used for all degenerate bases. These new primer and probe sequences identified take into consideration the available sequences of contemporary DENV lineages. Primers and probes are analyzed for homology to other known sequences using the Basic Local Alignment Search Tool (BLAST). Altschul S F, et al., *J Mol Biol*, 1990; 215: 403-410. These primers and probes, which are not identified by the Primer Express tool, are studied for possible amplification of DENV sequences. The identified primers and probes are compared to reference sequences as in Table 2 with the bold nucleotide representing a degenerate or non-wild type substitution.

TABLE 2

| | | Oligonucleotide |
|---|---|---|
| D1-F | Reference (24) | CAAAAGGAAGTCGTGCAATA (SEQ ID NO: 13) |
| | CDC DENV-1-4 Real Time RT-PCR | CAAAAGGAAGTCGYGCAATA (SEQ ID NO: 1) |
| D1-R | Reference (24) | CTGAGTGAATTCTCTCTACTGAAC (SEQ ID NO: 14) |
| | CDC DENV-1-4 Real Time RT-PCR | CTGAGTGAATTCTCTCTGCTRAAC (SEQ ID NO: 2) |
| D1-Probe | Reference (24) | CATGTGGTTGGGAGCACGC (SEQ ID NO: 15) |
| | CDC DENV-1-4 Real Time RT-PCR | CATGTGGYTGGGAGCRCGC (SEQ ID NO: 3) |
| D2-F | Reference (24) | CAGGTTATGGCACTGTCACGAT (SEQ ID NO: 16) |
| | CDC DENV-1-4 Real Time RT-PCR | CAGGCTATGGCACYGTCACGAT (SEQ ID NO: 4) |
| D2-R | Reference (24) | CCATCTGCAGCAACACCATCTC (SEQ ID NO: 17) |
| | CDC DENV-1-4 Real Time RT-PCR | CCATYTGCAGCARCACCATCTC (SEQ ID NO: 5) |
| D2-Probe | Reference (24) | CTCTCCGAGAACAGGCCTCGACTTCAA (SEQ ID NO: 18) |
| | CDC DENV-1-4 Real Time RT-PCR | CTCYCCRAGAACGGGCCTCGACTTCAA (SEQ ID NO: 6) |
| D3-F | Reference (24) | GGACTGGACACACGCACTCA (SEQ ID NO: 19) |
| | CDC DENV-1-4 Real Time RT-PCR | GGACTRGACACACGCACCCA (SEQ ID NO: 7) |
| D3-R | Reference (24) | CATGTCTCTACCTTCTCGACTTGTCT (SEQ ID NO: 20) |
| | CDC DENV-1-4 Real Time RT-PCR | CATGTCTCTACCTTCTCGACTTGYCT (SEQ ID NO: 8) |
| D3-Probe | Reference (24) | ACCTGGATGTCGGCTGAAGGAGCTTG (SEQ ID NO: 21) |
| | CDC DENV-1-4 Real Time RT-PCR | ACCTGGATGTCGGCTGAAGGAGCTTG (SEQ ID NO: 9) |
| D4-F | Reference (24) | TTGTCCTAATGATGCTGGTCG (SEQ ID NO: 22) |
| | CDC DENV-1-4 Real Time RT-PCR | TTGTCCTAATGATGCTRGTCG (SEQ ID NO: 10) |
| D4-R | Reference (24) | TCCACCTGAGACTCCTTCCA (SEQ ID NO: 23) |
| | CDC DENV-1-4 Real Time RT-PCR | TCCACCYGAGACTCCTTCCA (SEQ ID NO: 11) |
| D4-Probe | Reference (24) | TTCCTACTCCTACGCATCGCATTCCG (SEQ ID NO: 24) |
| | CDC DENV-1-4 Real Time RT-PCR | TYCCTACYCCTACGCATCGCATTCCG (SEQ ID NO: 12) |

The DENV-1 probe is labeled at the 5' end with the 6-carboxyfluorescein (FAM) reporter dye and at the 3' end with black hole quencher 1 (BHQ-1) fluorophore; the DENV-2 probe is labeled with HEX and BHQ-1; the DEN-3 probe is labeled with Texas red (TR) and BHQ-2; and the DEN-4 probe is labeled with Cy5 and BHQ-3. Genetic sequences from non DENV flaviviruses are used as controls.

RT-PCR is performed as follows: In singleplex reaction mixtures, 5 µl of RNA are combined with 25 pmol of each primer and 4.5 pmol of the probe in a 25 µl total volume reaction using Superscript III One Step RT-PCR (Invitrogen, Carlsbad, Calif.). Each reaction mixture contains a single DENV serotype primer pair (with degenerate sequence) and probe (with degenerate sequence); therefore, in singleplex assays, four separate reactions are carried out for each RNA sample. In fourplex reaction mixtures (e.g. multiplex), 5 µl of RNA are combined with 25 pmol of each primer of DENV-1 and DENV-3, 12.5 pmol of each primer of DENV-2 and DENV-4 (each), and 4.5 pmol of each respective probe (primers and probes used are listed in Table 2) in a 25 µl volume total reaction mixture. Reverse transcription of 30 min at 50° C. is followed by 45 cycles of amplification in an ABI 7500 Dx (Applied Biosystems, Foster City, Calif.) according to Invitrogen Superscript instructions for real-time RT-PCR conditions and using a 60° C. annealing temperature.

Identification of Limit of Detection (LOD)

The CDC DENV-1-4 assay limit of detection (LoD) is determined using a panel of quantified (pfu/mL) stocks of laboratory strain infectious DENV-1, -2, -3 and -4 diluted in human serum or plasma with eight (8) 1:10 dilutions; 5 replicas per dilution. Viral RNA from every replica sample is extracted and tested using the protocol above. The assay is run with a quantitative component in order to compare the different versions of the assay with improved accuracy. The LoD of the assay is defined as the last dilution in which virus is detected in 100% of the replicas. Virus detection, measured in genome copy equivalents per mL of sample (GCE/mL) is compared between virus dilutions in human serum and human plasma and the results illustrated in FIG. 1A (singleplex) and 1B (multiplex). Equivalent detection of DENV serotypes is achieved in both, singleplex and multiplex formats of the assay diluted in serum or plasma. The LoD is measured at approximately $1 \times 10^4$ GCE/mL in both formats, which corresponds to titers of approximately $1 \times 10^3$ pfu/mL.

Broad Recognition of DENV Strains

The assay is further tested on 29 DENV-1-4 cultured and quantified clinical isolates obtained from international locations in order to confirm that the chosen assay conditions above will broadly recognize DENV strains from a broad geographical distribution of sources. Quantified stocks are serially diluted in human serum at 1:10 dilutions down to $1 \times 10^2$ pfu/mL in triplicate. A similar LoD is determined in all cultured clinical isolates as is illustrated in Table 3 depicting the year of the infection's source, the location the sample was taken, and the genotype of the DENV strain.

TABLE 3

| Serotype | Year | Country | Genotype | $10^3$ pfu/ml Rate Pos | $10^2$ pfu/ml Rate Pos |
|---|---|---|---|---|---|
| DENV-1 | 2003 | Brazil | African/American | 3/3 | 0/3 |
| DENV-1 | 2007 | Mexico | African/American | 3/3 | 0/3 |
| DENV-1 | 2007 | Venezuela | African/American | 3/3 | 0/3 |
| DENV-1 | 1994 | Sri Lanka | South Pacific | 3/3 | 0/3 |
| DENV-1 | 2004 | Philippines | South Pacific | 3/3 | 0/3 |
| DENV-1 | 2004 | Thailand | Asian | 3/3 | 0/3 |
| DENV-1 | 2006 | Thailand | Asian | 3/3 | 0/3 |
| DENV-2 | 2006 | Brazil | SE Asian/American | 3/3 | 0/3 |
| DENV-2 | 2007 | Colombia | SE Asian/American | 3/3 | 0/3 |
| DENV-2 | 1980 | Ivory Coast | Sylvatic | 3/3 | 2/3 |
| DENV-2 | 1988 | Viet Nam | Asian II | 3/3 | 1/3 |
| DENV-2 | 2006 | Thailand | Asian II | 3/3 | 0/3 |
| DENV-2 | 2003 | Dominican R. | SE Asian/American | 3/3 | 1/3 |
| DENV-2 | 2003 | Costa Rica | SE Asian/American | 3/3 | 0/3 |
| DENV-2 | 1996 | Peru | American | 3/3 | 1/3 |

TABLE 3-continued

| Serotype | Year | Country | Genotype | $10^3$ pfu/ml Rate Pos | $10^2$ pfu/ml Rate Pos |
|---|---|---|---|---|---|
| DENV-2 | 1982 | Burkina Faso | Cosmopolitan | 3/3 | 1/3 |
| DENV-2 | 2006 | India | Cosmopolitan | 3/3 | 0/3 |
| DENV-3 | 2006 | Puerto Rico | Indian Subcont. | 3/3 | 0/3 |
| DENV-3 | 2003 | Brazil | Indian Subcont. | 3/3 | 1/3 |
| DENV-3 | 1995 | Samoa | South Pacific | 3/3 | 0/3 |
| DENV-3 | 2006 | Thailand | Thailand | 3/3 | 0/3 |
| DENV-3 | 2000 | Ecuador | Indian Subcont. | 3/3 | 1/3 |
| DENV-3 | 1991 | Cook Island | South Pacific | 3/3 | 0/3 |
| DENV-4 | 2006 | Colombia | Indonesian | 3/3 | 0/3 |
| DENV-4 | 2006 | Mexico | Indonesian | 3/3 | 0/3 |
| DENV-4 | 1992 | Sri Lanka | SE Asian | 3/3 | 1/3 |
| DENV-4 | 2006 | Thailand | SE Asian | 3/3 | 0/3 |
| DENV-4 | 1994 | St. Croix | Indonesian | 3/3 | 0/3 |
| DENV-4 | 1999 | Ecuador | Indonesian | 3/3 | 1/3 |
| DENV-4 | 1995 | Micronesia | SE Asian | 3/3 | 0/3 |

Cross Reactivity

The assay above is further evaluated for analytical specificity by testing with nucleic acids extracted from 12 organisms representing common pathogens present in the blood of patients with febrile illness. The above assay is performed on all 12 samples in triplicate. All negative samples test negative for DENV (Table 4). Only the samples spiked with DENV test positive indicating that the assay presents no cross-reactivity with any pathogen tested at clinically relevant concentrations.

TABLE 4

| Pathogen | Sample type | Concentration | DENV RT-PCR Rate positive |
|---|---|---|---|
| Virus |  | pfu/ml |  |
| DENV-1 | spiked serum | $1 \times 10^6$ | 3/3 |
| DENV-2 | spiked serum | $1 \times 10^6$ | 3/3 |
| DENV-3 | spiked serum | $1 \times 10^6$ | 3/3 |
| DENV-4 | spiked serum | $1 \times 10^6$ | 3/3 |
| WNV | spiked serum | $6.9 \times 10^7$ | 0/3 |
| YFV | spiked serum | $3.7 \times 10^6$ | 0/3 |
| SLEV | spiked serum | $3.7 \times 10^6$ | 0/3 |
| CHIKV | spiked serum | $4.0 \times 10^6$ | 0/3 |
| HCV | clinical serum | unknown | 0/3 |
| HAV | clinical serum | unknown | 0/3 |
| HSV-1 | spiked serum | $1.0 \times 10^5$ | 0/3 |
| HSV-2 | spiked serum | $1.0 \times 10^5$ | 0/3 |
| CMV | spiked serum | $1.0 \times 10^5$ | 0/3 |
| VZV | spiked serum | $1.0 \times 10^5$ | 0/3 |
| Bacteria |  | bacteria/ml |  |
| Leptospiro | spiked serum | $2.5 \times 10^5$ | 0/3 |
| Borrelia burgdorferi | spiked serum | $1.0 \times 10^6$ | 0/3 |

Interference with Potentially Contaminating Sample Materials

The assay above is evaluated in the presence of normal human serum (NHS) or in NHS containing bilirubin, cholesterol, hemoglobin, triglycerides, or genomic DNA. Every interference study is performed in the presence of cultured and quantified (pfu/mL) stocks of infectious laboratory strain DENV-1-4 diluted to concentrations 1:10 above the LoD dilution ($1 \times 10^4$ pfu/ml), equal to the LoD dilution ($1 \times 10^3$ pfu/ml), and the 1:10 dilution below the LoD ($1 \times 10^2$ pfu/ml). No significant interference in DENV detection is observed in the presence of any of the potential human endogenous interfering biomolecules tested.

Carryover or Cross-Contamination Studies

A panel of DENV-1-4 diluted to high-positive ($10^7$ pfu/ml) and high-negative ($5 \times 10^2$ pfu/ml) concentrations are used to determine sensitivity of the above assay to cross contamination. Eight high-positive and 8 high-negative replicas are tested in an alternating series. Viral RNA from every replica sample is extracted using the Qiagen QIAamp® DSP Viral RNA Mini Kit and the assay is performed as above. All negative samples test negative (32/32) and all DENV positive samples test positive for DENV (32/32) indicating no observed cross contamination.

Effect of Sample Freeze/Thaw on Assay Detection Ability

Figure 2:
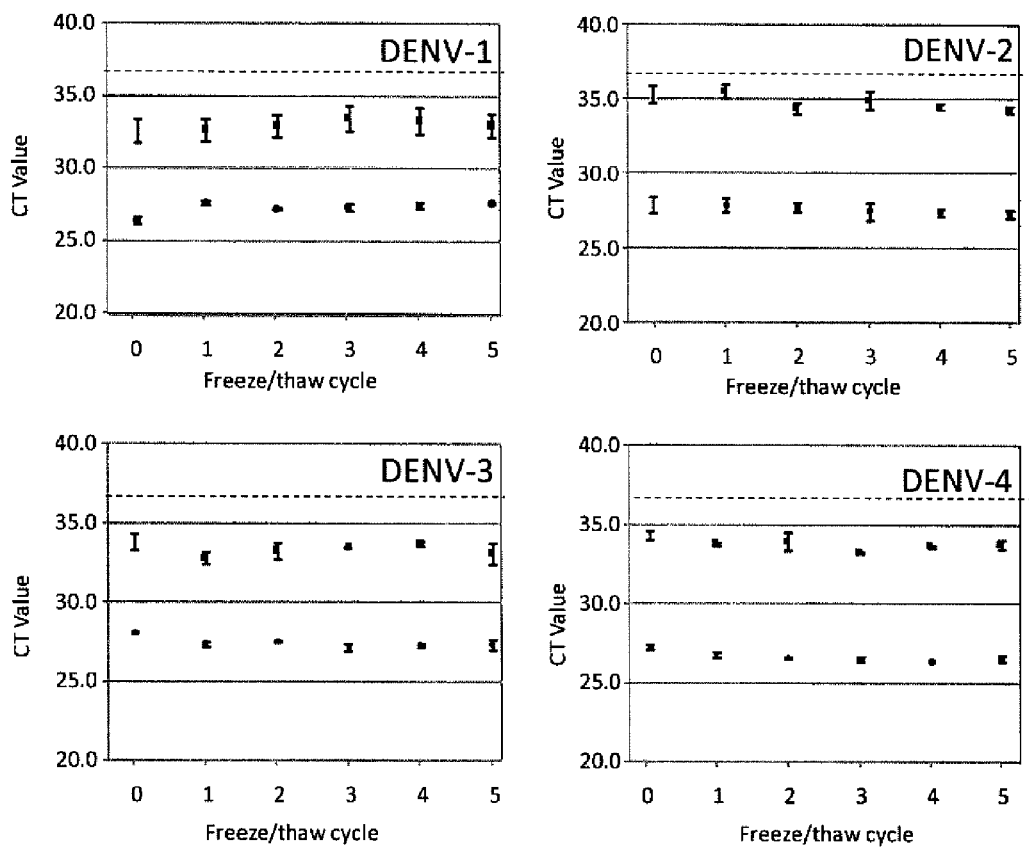
FIG. 2 represents the ability of the assay to detect DENV serotypes following multiple freeze/thaw cycles.

Effects of temperature variation on the above assay performance are evaluated by comparing detection of DENV spiked human serum samples after multiple freeze/thaw cycles using the above assay procedure. Moderate and low positive dilutions are prepared in triplicate and frozen at −80° C. for 24 hours and then subjected to five consecutive freeze/thaw cycles. Once thawed, every sample is processed accordingly. This validation determined a 100% qualitative agreement between the initial and post freeze/thaw cycle (1, 2, 3, 4, and 5) detection results as illustrated in FIG. 2.

Example 2

Assay for Presence of DENV in Biological Samples from Clinical Sources

The ability of the DENV assay of Example 1 to detect DENV using extracted RNA from serum obtained from either control subjects or from subjects diagnosed as DENV positive by serological assays is evaluated. The RT-PCR assay of Example 1 is used to examine each of the samples for the presence or absence of DENV. Results are illustrated in Table 5 where the degenerate and other non-wild-type substitutions are highlighted in bold.

TABLE 5

| Oligonucleotide | | | Frequency | Position | Gene | Amplicon size |
|---|---|---|---|---|---|---|
| D1-F | Reference (24) | CAAAAGGAAGTCGTGCAATA (SEQ ID NO: 13) | 12/16 | 8936-8955 | NS5 | 112 bp |
| | CDC DENV-1-4 Real Time RT-PCR | CAAAAGGAAGTCGYGCAATA (SEQ ID NO: 1) | 16/16 | | | |
| D1-R | Reference (24) | CTGAGTGAATTCTCTACTGAAC (SEQ ID NO: 14) | 3/16 | 9023-9047 | NS5 | 112 bp |
| | CDC DENV-1-4 Real Time RT-PCR | CTGAGTGAATTCTCTCTGCTRAAC (SEQ ID NO: 2) | 16/16 | | | |
| D1-Probe | Reference (24) | CATGTGGTTGGGAGCACGC (SEQ ID NO: 15) | 4/16 | 8961-8979 | NS5 | 112 bp |
| | CDC DENV-1-4 Real Time RT-PCR | CATGTGGYTGGGAGCRCGC (SEQ ID NO: 3) | 16/16 | | | |
| D2-F | Reference (24) | CAGGTTATGGCACTGTCACGAT (SEQ ID NO: 16) | 0/16 | 1426-1447 | E | 78 bp |
| | CDC DENV-1-4 Real Time RT-PCR | CAGGCTATGGCACYGTCACGAT (SEQ ID NO: 4) | 13/16 | | | |
| D2-R | Reference (24) | CCATCTGCAGCAACACCATCTC (SEQ ID NO: 17) | 3/16 | 1482-1504 | E | 78 bp |
| | CDC DENV-1-4 Real Time RT-PCR | CCATYTGCAGCARCACCATCTC (SEQ ID NO: 5) | 16/16 | | | |
| D2-Probe | Reference (24) | CTCTCCGAGAACAGGCCTCGACTTCAA (SEQ ID NO: 18) | 10/16 | 1454-1480 | E | 78 bp |
| | CDC DENV-1-4 Real Time RT-PCR | CTCYCCRAGAACGGGCCTCGACTTCAA (SEQ ID NO: 6) | 14/16 | | | |
| D3-F | Reference (24) | GGACTGGACACACGCACTCA (SEQ ID NO: 19) | 9/15 | 701-720 | prM | 74 bp |
| | CDC DENV-1-4 Real Time RT-PCR | GGACTRGACACACGCACCCA (SEQ ID NO: 7) | 15/15 | | | |
| D3-R | Reference (24) | CATGTCTCTACCTTCTCGACTTGTCT (SEQ ID NO: 20) | 5/15 | 749-775 | prM | 74 bp |
| | CDC DENV-1-4 Real Time RT-PCR | CATGTCTCTACCTTCTCGACTTGYCT (SEQ ID NO: 8) | 15/15 | | | |
| D3-Probe | Reference (24) | ACCTGGATGTCGGCTGAAGGAGCTTG (SEQ ID NO: 21) | 14/15 | 722-747 | prM | 74 bp |
| | CDC DENV-1-4 Real Time RT-PCR | ACCTGGATGTCGGCTGAAGGAGCTTG (SEQ ID NO: 9) | 14/15 | | | |
| D4-F | Reference (24) | TTGTCCTAATGATGCTGGTCG (SEQ ID NO: 22) | 4/7 | 884-904 | prM | 89 bp |
| | CDC DENV-1-4 Real Time RT-PCR | TTGTCCTAATGATGCTRGTCG (SEQ ID NO: 10) | 7/7 | | | |
| D4-R | Reference (24) | TCCACCTGAGACTCCTTCCA (SEQ ID NO: 23) | 5/7 | 953-973 | prM | 89 bp |
| | CDC DENV-1-4 Real Time RT-PCR | TCCACCYGAGACTCCTTCCA (SEQ ID NO: 11) | 7/7 | | | |

TABLE 5-continued

| Oligonucleotide | | Frequency | Position | Gene | Amplicon size |
|---|---|---|---|---|---|
| D4-Probe | Reference (24) TTCCTACTCCTACGCATCGCATTCCG (SEQ ID NO: 24) | 4/7 | 939-965 | prM | 89 bp |
| | CDC DENV-1-4 Real Time RT-PCR TYCCTACYCCTACGCATCGCATTCCG (SEQ ID NO: 12) | 7/7 | | | |

Briefly, the primers and probes of SEQ ID NOs: 1-12 show great superiority in their capability to recognize each DENV serotype as illustrated by far superior frequency of recognition of the target virus. For the first time, this assay is robust enough to be used in a detection assay whereby a positive result demonstrates diagnosis of DENV infection in a subject, and the absence of a positive result diagnoses the absence of DENV infection in the subject.

Example 3

Detection of DENV is Clinical Samples in a Prospective Study

A total of 86 acute serum samples are collected from dengue-suspected, febrile patients (0-5 days of symptoms; AVG age 14.3, 42% F) at 3 different public health laboratories (2009-2011). Fifty (50) serum samples are obtained through the dengue fever passive surveillance system administered by the CDC Dengue Branch: 25 of these serum samples are tested at the CDC Dengue Branch Laboratory and 25 serum samples are decoded, sent to, and tested at the Puerto Rico Department of Health. Thirty six (36) serum samples are obtained as part of a national surveillance and reference program in Costa Rica. Samples are received by the National Laboratory in Costa Rica and decoded before testing. All three laboratories follow the same protocol: viral RNA is extracted using the Qiagen QIAamp® DSP Viral RNA Mini Kit (cat#61904) following the manufacturer's protocol. The eluted viral RNA is tested by the assay of Example 1 using the primers and probes of Table 1. To confirm diagnosis, the DENV envelope gene is sequenced on all 86 samples using bi-directional Sanger sequencing. Applying sequence data as a reference method, the assay achieved a 97.92% positive agreement and 100% negative agreement (Table 6). The prospective samples are not complemented by a second, convalescent specimen.

TABLE 6

Multiplex CDC DENV-1-4 Real-Time RT-PCR Assay Comparison Results

| | | Reference Method (Sequencing) | | |
|---|---|---|---|---|
| | | Positive | Negative | Total |
| CDC DENV-1-4 Real-Time RT-PCR Assay | Positive | 47 | 0 | 47 |
| | Negative | 1* | 38 | 39 |
| | Total | 48 | 38 | 86 |
| | | Value | 95% Confidence Interval | |
| Positive percent agreement | | 97.92% | 89.10-99.63 | |
| Negative percent agreement | | 100% | 90.82-100 | |

Example 4

Detection of DENV is Clinical Samples in a Retrospective Study

The assay of Example 1 is further evaluated using retrospective clinical samples obtained from the archived CDC routine dengue surveillance specimens collected in pairs (2007-2011). Acute samples were collected during the first five days of symptoms, and convalescent sample was collected at least 6 days after the onset of symptoms. These samples are tested with the IgM Capture Enzyme Linked Immunosorbent Assay (CDC MAC-ELISA—validated in-house) in order to establish seroconversion. A total of 371 acute samples: 39 dengue-positive international samples, 82 dengue-positive samples from the Puerto Rico dengue surveillance system, and an additional 250 dengue-negative samples (no IgM conversion), also from Puerto Rico, are included in the test. The percent (%) agreement between the result using the assay of Example 1 and the IgM conversion is calculated for the number of samples that received positive or negative results and the results presented in Table 7. In addition, bi-directional Sanger sequencing of the DENV E gene is performed to corroborate CDC DENV-1-4 Real-Time RT-PCR positive detection and serotyping results.

TABLE 7

Multiplex CDC DENV-1-4 Real-Time RT-PCR Assay Comparison Results

| | | Reference Method (IgM Conversion)† | | |
|---|---|---|---|---|
| | | Positive | Negative | Total |
| CDC DENV-1-4 Real-Time RT-PCR Assay | Positive | 100* | 4*** | 104 |
| | Negative | 2** | 265 | 267 |
| | Total | 102 | 269 | 371 |
| | | Value | 95% Confidence Interval | |
| Positive percent agreement | | 98.04% | 93.13-99.46 | |
| Negative percent agreement | | 98.51% | 96.24-99.42 | |

Example 5

Detection of DENV by PCR/LC/MS

The samples of Example 2 are each rescreened using RT-PCR amplification with parameters similar to the RT-PCR assay of Example 1. The reaction products are subjected to analyses by electrospray ionization mass spectrometry substantially as described by Naito, Y, et al., *Rapid Communications in Mass Spectrometry*, 1995; 9:1484-1486; or Wunschel D S, et al., *Rapid Commun Mass Spectral.*

1996; 10(1):29-35. Each of the reaction products from the PCR reactions are successfully and rapidly detected.

Example 6

Detection of DENV by PCR/Gel Electrophoresis

Samples of Example 2 are each rescreened using PCR amplification with parameters similar to the RT-PCR assay of Example 1. The amplified reaction products are separated by gel electrophoresis and detected by fluorescent imaging. Each of the primer pairs and probes show detectable amplified DENV.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in A Guide to Methods and Applications Academic Press, NY.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Various modifications of the present invention, in addition to those shown and described herein, will be apparent to those skilled in the art of the above description. Such modifications are also intended to fall within the scope of the appended claims.

REFERENCE LIST

1. Alexander, N., A. Balmaseda, I. C. Coelho, E. Dimaano, T. T. Hien, N. T. Hung, T. Janisch, A. Kroeger, L. C. Lum, E. Martinez, J. B. Siqueira, T. T. Thuy, I. Villalobos, E. Villegas, B. Wills, and W. H. O. s. D. S. G. on behalf of the European Union. 2011. Multicentre prospective study on dengue classification in four South-east Asian and three Latin American countries. Trop Med Int Health.
2. Ayala, A., A. Rivera, M. Johansson, and J. L. Muñoz-Jordán. 2006. Travel-Associated Dengue—United States, 2005. MMWR 55:700-702.
3. Bessoff, K., M. Delorey, W. Sun, and E. Hunsperger. 2008. Comparison of two commercially available dengue virus (DENV) NS1 capture enzyme-linked immunosorbent assays using a single clinical sample for diagnosis of acute DENV infection. Clin Vaccine Immunol 15:1513-1518.
4. Brunkard, J. M., J. L. Robles Lopez, J. Ramirez, E. Cifuentes, S. J. Rothenberg, E. A. Hunsperger, C. G. Moore, R. M. Brussolo, N. A. Villarreal, and B. M. Haddad. 2007. Dengue Fever Seroprevalence and Risk Factors, Texas-Mexico Border, 2004. Emerg Infect Dis 13:1477-1483.
5. Callahan, J. D., S. J. Wu, A. Dion-Schultz, B. E. Mangold, L. F. Peruski, D. M. Watts, K. R. Porter, G. R. Murphy, W. Suharyono, C. C. King, C. G. Hayes, and J. J. Temenak. 2001. Development and evaluation of serotype- and group-specific fluorogenic reverse transcriptase PCR (TaqMan) assays for dengue virus. J Clin Microbiol 39:4119-4124.
6. Centers for Disease, C., and Prevention. 2010. Locally acquired Dengue—Key West, Fla., 2009-2010. MMWR. Morbidity and mortality weekly report 59:577-581.
7. Chau, T. N., K. L. Anders, B. Lien le, N. T. Hung, L. T. Hieu, N. M. Tuan, T. T. Thuy, T. Phuong le, N. T. Tham, M. N. Lanh, J. J. Farrar, S. S. Whitehead, and C. P. Simmons. 2010. Clinical and virological features of Dengue in Vietnamese infants. PLoS Negl Trop Dis 4:e657.
8. Chien, L. J., T. L. Liao, P. Y. Shu, J. H. Huang, D. J. Gubler, and G. J. Chang. 2006. Development of real-time reverse transcriptase PCR assays to detect and serotype dengue viruses. J Clin Microbiol 44:1295-1304.
9. Condon, R., G. Taleo, T. Stewart, T. Sweeney, and T. Kiedrzynski. 2000. Dengue surveillance in the Pacific Islands. Pacific health dialog 7:122-126.
10. Descloux, E., V. M. Cao-Lormeau, C. Roche, and X. De Lamballerie. 2009. Dengue 1 diversity and microevolution, French Polynesia 2001-2006: connection with epidemiology and clinics. PLoS Negl Trop Dis 3:e493.
11. Dussart, P., L. Petit, B. Labeau, L. Bremand, A. Leduc. D. Moua, S. Matheus, and L. Baril. 2008. Evaluation of Two New Commercial Tests for the Diagnosis of Acute Dengue Virus Infection Using NS1 Antigen Detection in Human Serum. PLoS Negl Trop Dis 2:e280.
12. Effler, P. V., L. Pang, P. Kitsutani, V. Vorndam, M. Nakata, T. Ayers, J. Elm, T. Torn, P. Reiter, J. G. Rigau-Perez, J. M. Hayes, K. Mills, M. Napier, G. G. Clark, and D. J. Gubler. 2005. Dengue fever, Hawaii, 2001-2002. Emerg Infect Dis 11:742-749.
13. Franco, C., N. A. Hynes, N. Bouri, and D. A. Henderson. 2010. The dengue threat to the United States. Biosecurity and bioterrorism: biodefense strategy, practice, and science 8:273-276.
14. Gomes, A. L., A. M. Silva, M. T. Cordeiro, G. F. Guimaraes, E. T. Marques, Jr., and F. G. Abath. 2007. Single-tube nested PCR using immobilized internal primers for the identification of dengue virus serotypes. J Virol Methods 145:76-79.
15. Gregory, C. J., L. M. Santiago, D. F. Arguello, E. Hunsperger, and K. M. Tomashek. 2010. Clinical and laboratory features that differentiate dengue from other febrile illnesses in an endemic area—Puerto Rico, 2007-2008. Am J Trop Med Hyg 82:922-929.
16. Gregory, C. J., and K. M. Tomashek. 2012. Management of severe dengue. Pediatr Crit Care Med 13:125; author reply 125-126.
17. Gubler, D. J. 2002. Epidemic dengue/dengue hemorrhagic fever as a public health, social and economic problem in the 21st century. Trends Microbiol 10:100-103.
18. Gubler, D. J., G. Kuno, G. E. Sather, M. Velez, and A. Oliver. 1984. Mosquito cell cultures and specific monoclonal antibodies in surveillance for dengue viruses. Am J Trop Med Hyg 33:158-165.

19. Gubler, D. J., W. Suharyono, I. Lubis, S. Eram, and S. Gunarso. 1981. Epidemic dengue 3 in central Java, associated with low viremia in man. Am J Trop Med Hyg 30:1094-1099.
20. Henchal, E. A., S. L. Polo, V. Vorndam, C. Yaemsiri, B. L. Innis, and C. H. Hoke. 1991. Sensitivity and specificity of a universal primer set for the rapid diagnosis of dengue virus infections by polymerase chain reaction and nucleic acid hybridization. Am J Trop Med Hyg 45:418-428.
21. Holmes, E. C., and S. S. Twiddy. 2003. The origin, emergence and evolutionary genetics of dengue virus. Infect Genet Evol 3:19-28.
22. Hsieh, C. J., and M. J. Chen. 2009. The commercial dengue NS1 antigen-capture ELISA may be superior to IgM detection, virus isolation and RT-PCR for rapid laboratory diagnosis of acute dengue infection based on a single serum sample. J Clin Virol 44:102.
23. Huhtamo, E., E. Hasu, N.Y. Uzcategui, E. Erra, S, Nikkari, A. Kantele, O. Vapalahti, and H. Piiparinen. 2010. Early diagnosis of dengue in travelers: comparison of a novel real-time RT-PCR, NS1 antigen detection and serology. J Clin Virol 47:49-53.
24. Johnson, B. W., B. J. Russell, and R. S. Lanciotti. 2005. Serotype-specific detection of dengue viruses in a fourplex real-time reverse transcriptase PCR assay. J Clin Microbiol 43:4977-4983.
25. Lanciotti, R. S. 2003. Molecular amplification assays for the detection of flaviviruses. Adv Virus Res 61:67-99.
26. Leitmeyer, K. C., D. W. Vaughn, D. M. Watts, R. Salas, I. Villalobos, C. de, C. Ramos, and R. Rico-Hesse. 1999. Dengue virus structural differences that correlate with pathogenesis. J Virol 73:4738-4747.
27. Low, J. G., A. Ong, L. K. Tan, S. Chaterji, A. Chow, W. Y. Lim, K. W. Lee, R. Chua, C. R. Chua, S. W. Tan, Y. B. Cheung, M. L. Hibberd, S. G. Vasudevan, L. C. Ng, Y. S. Leo, and E. E. Ooi. 2011. The early clinical features of dengue in adults: challenges for early clinical diagnosis. PLoS Negl Trop Dis 5:e1191.
28. McElroy, K. L., G. A. Santiago, N. J. Lennon, B. W. Birren, M. R. Henn, and J. L. Munoz-Jordan. 2011. Endurance, refuge, and reemergence of dengue virus type 2, Puerto Rico, 1986-2007. Emerg Infect Dis 17:64-71.
29. Mohammed, H., M. Ramos, J. Armstrong, J. Munoz-Jordan, K. O. Arnold-Lewis, A. Ayala, G. G. Clark, E. S. Tull, and M. E. Beatty. 2010. An outbreak of dengue fever in St. Croix (US Virgin Islands), 2005. PLoS One 5:e13729.
30. Mohammed, H. P., M. M. Ramos, A. Rivera, M. Johansson, J. L. Munoz-Jordan, W. Sun, and K. M. Tomashek. 2008. Travel-associated dengue infections in the United States, 1996 to 2005. J Travel Med 17:8-14.
31. Munoz-Jordan, J. L., C. S. Collins, E. Vergne, G. A. Santiago, L. Petersen, W. Sun, and J. M. Linnen. 2009. Highly sensitive detection of dengue virus nucleic acid in samples from clinically ill patients. J Clin Microbial 47:927-931.
32. Organization, W. H. 2009. Dengue guidelines for diagnosis, treatment, prevention and control. Geneva http://whqlibdoc.who.int/publications/2009/9789241547871_eng.pdf.
33. Radke, E. G., C. J. Gregory, K. W. Kintziger, E. K. Sauber-Schatz, E. A. Hunsperger, G. R. Gallagher, J. M. Barber, B. J. Biggerstaff, D. R. Stanek, K. M. Tomashek, and C. G. Blackmore. 2012. Dengue outbreak in key west, Florida, USA, 2009. Emerg Infect Dis 18:135-137.
34. Ramos, M. M., H. Mohammed, E. Zielinski-Gutierrez, M. H. Hayden, J. L. Lopez, M. Fournier, A. R. Trujillo, R. Burton, J. M. Brunkard, L. Anaya-Lopez, A. A. Banicki, P. K. Morales, B. Smith, J. L. Munoz-Jordan, and S. H. Waterman. 2008. Epidemic Dengue and Dengue Hemorrhagic Fever at the Texas-Mexico Border: Results of a Household-based Seroepidemiologic Survey, December 2005. Am J Trop Med Hyg 78:364-369.
35. Rico-Hesse, R. 2007. Dengue virus evolution and virulence models. Clin Infect Dis 44:1462-1466.
36. Rico-Hesse, R. 1990. Molecular evolution and distribution of dengue viruses type 1 and 2 in nature. Virology 174:479-493.
37. Rigau-Perez, J. G., A. Ayala-Lopez, E. J. Garcia-Rivera, S. M. Hudson, V. Vorndam, P. Reiter, M. P. Cano, and G. G. Clark. 2002. The reappearance of dengue-3 and a subsequent dengue-4 and dengue-1 epidemic in Puerto Rico in 1998. Am J Trop Med Hyg 67:355-362.
38. Sanchez-Seco, M. P., D. Rosario, L. Hernandez, C. Domingo, K. Valdes, M. G. Guzman, and A. Tenorio. 2006. Detection and subtyping of dengue 1-4 and yellow fever viruses by means of a multiplex RT-nested-PCR using degenerated primers. Trop Med Int Health 11:1432-1441.
39. Sharp, T. M., P. Pillai, E. Hunsperger, G. A. Santiago, T. Anderson, T. Vap, J. Collinson, B. F. Buss, T. J. Safranek, M. J. Sotir, E. S. Jentes, J. L. Munoz-Jordan, and D. F. Arguello. 2012. A cluster of dengue cases in American missionaries returning from Haiti, 2010. Am J Trap Med Hyg 86:16-22.
40. Steel, A., D. J. Gubler, and S. N. Bennett. 2010. Natural attenuation of dengue virus type-2 after a series of island outbreaks: a retrospective phylogenetic study of events in the South Pacific three decades ago. Virology 405:505-512.
41. Thomas, L., V. Moravie, F. Besnier, R. Valentino, S. Kaidomar, L. V. Coquet, F. Najioullah, F. Lengelle, R. Cesaire, A. Cabie, and D. Working Group on. 2012. Clinical presentation of dengue among patients admitted to the adult emergency department of a tertiary care hospital in Martinique: implications for triage, management, and reporting. Ann Emerg Med 59:42-50.
42. Tomashek, K. M., A. Rivera, J. L. Munoz-Jordan, E. Hunsperger, L. Santiago, O. Padro, E. Garcia, and W. Sun. 2009. Description of a large island-wide outbreak of dengue in Puerto Rico, 2007. Am J Trop Med Hyg 81:467-474.
43. Tricou, V., N. N. Minh, J. Farrar, H. T. Tran, and C. P. Simmons. 2011. Kinetics of viremia and NS1 antigenemia are shaped by immune status and virus serotype in adults with dengue. PLoS Negl Trop Dis 5:e1309.
44. Twiddy, S. S., J. J. Farrar, N. Vinh Chau, B. Wills, E. A. Gould, T. Gritsun, G. Lloyd, and E. C. Holmes. 2002. Phylogenetic relationships and differential selection pressures among genotypes of dengue-2 virus. Virology 298:63-72.
45. World-Health-Organization. 2010. Impact of Dengue. http://www.who.int/csr/disease/dengue/impact/en/index.html.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An isolated mixture of oligonucleotides comprising the sequence of: SEQ ID NO: 3; SEQ ID NO: 6; or SEQ ID NO: 12; at least one of the mixture further comprising a fluorescent label.

* * * * *